United States Patent [19]

Leonard et al.

[11] 4,124,633
[45] Nov. 7, 1978

[54] TELLURIUM CATALYZED DECOMPOSITION OF PEROXIDE INTERMEDIATES RESULTING FROM THE AUTOXIDATION OF UNSATURATED ALDEHYDES

[75] Inventors: John J. Leonard, Springfield, Pa.; Jar-lin Kao, Cherry Hill, N.J.

[73] Assignee: Atlantic Richfield Company, Los Angeles, Calif.

[21] Appl. No.: 820,996

[22] Filed: Aug. 1, 1977

[51] Int. Cl.$^2$ ............................................. C07C 51/32
[52] U.S. Cl. ..................................... 562/598; 562/533
[58] Field of Search ........................ 260/530 N, 526 N

[56] References Cited

U.S. PATENT DOCUMENTS 2,212,900  8/1940  Groll et al. ..................... 260/530 N

FOREIGN PATENT DOCUMENTS 373,326  5/1932  United Kingdom ................ 260/530 N

*Primary Examiner*—Vivian Garner
*Attorney, Agent, or Firm*—Delbert E. McCaslin

[57] ABSTRACT

A process for the preparation of acrylic acid or methacrylic acid which comprises catalytically decomposing or converting in the presence of tellurium the peroxide (peroxy) compounds contained in the oxidate solution derived from the autoxidation of acrolein or methacrolein, particularly, the conversion of permethacrylic acid and methacrolein monopermethacrylate to methacrylic acid.

12 Claims, No Drawings

TELLURIUM CATALYZED DECOMPOSITION OF PEROXIDE INTERMEDIATES RESULTING FROM THE AUTOXIDATION OF UNSATURATED ALDEHYDES

BACKGROUND OF THE INVENTION

When α,β-unsaturated aliphatic aldehydes such as acrolein or methacrolein are oxidized in the liquid phase with oxygen or an oxygen-containing gas such as air, peroxide (peroxy) compounds are co-produced along with the corresponding α,β-unsaturated carboxylic acids. A mixture of products are obtained in the resulting oxidate solution formed by the oxidation. Based on the total weight, the oxidate solution will generally contain unreacted aldehyde of from 20 to 70 weight per cent, and from 40 to 10 weight per cent of the corresponding acrylic or methacrylic acid product as well as peroxide (peroxy) compounds of the unsaturated aldehyde feed materials and perioxide (peroxy) compounds of the unsaturated acid product and other by-products. The unsaturated peroxide (peroxy) compounds co-produced during the autoxidation of acrolein and methacrolein to acrylic acid and methacrylic acid would be peracrylic acid and acrolein monoperacrylate and permethacrylic acid and methacrolein monopermethacrylate respectively.

The present invention relates to a process for the tellurium catalyzed conversion or decomposition of the above described unsaturated peroxide compounds formed by the autoxidation of the unsaturated aldehydes (acrolein and methacrolein). The tellurium catalyzed conversion or decomposition is carried out after the autoxidation stage is completed. Employment of the tellurium catalyst during the oxidation step of the aldehyde does not successfully provide an in situ conversion of the intermediate peroxide compounds to the desired acid product. The oxidate product solution of the autoxidation of an aldehyde containing the mixture of products as hereinabove described may be treated according to the process of this invention; the process to catalytically decompose the peroxides being carried out after the aldehyde has been oxidized and the intermediate peroxide compounds formed. Conversion of the peroxide compounds according to this invention provides for a high selectivity to the acid and for the recovery of large percentages of the desired unsaturated carboxylic acid (acrylic or methacrylic) as well as a minimum amount of polymer formation, resulting in high overall yield of the acid from the particular original unsaturated aldehyde as compared to prior art processes, including straight thermal decomposition of peroxide compounds. Catalytic decomposition of the oxidate by the process of the invention gives peroxide conversions that are substantially complete and provides a high selectivity to methacrylic or acrylic acid.

Generally the oxidation of unsaturated aliphatic aldehydes to the corresponding acid in the liquid phase has been difficult due to polymerization of the unsaturated acids when formed and the co-production of various undesirable peroxides of the unsaturated acids and aldehydes formed during oxidation, resulting in low selectivity to and yield of the unsaturated acids.

U.S. Pat. No. 3,144,769 in an attempt to prevent polymeric by-products, describes a liquid phase process for the oxidation of methacrolein or acrolein to the corresponding acid and peroxide compounds in the presence of molecular oxygen and a small quantity of iodine. The products of the oxidation contained mixtures of unsaturated acids, and large amounts of both acid and aldehyde peroxides and unreacted aldehyedes. After separation the peroxide products were separately decomposed to the corresponding unsaturated acid by subjecting the oxidate containing the peroxides to the catalytic effect of a protonic acid such as p-toluene sulfonic acid and an alcohol forming a hot solvent solution as is further described in U.S. Pat. No. 3,253,025.

In an article by William F. Brill and Fred Lister, Journal of Organic Chemistry, VOl. 26, pp. 565–569, 1961 the metal-salt catalyzed oxidation of methacrolein in acetic acid is described. The methacrolein goes to peroxide products, acid and major amounts of soluble polymer.

An article by Benjamin Phillips, et al, Journal of the American Chemical Society, Vol. 76, pp. 5982–5986, 1957 shows the preparation of peracetic acid by the autoxidation of acetaldehyde and with peracetic acid and acetaldehyde monoperacetate as intermediates. At temperatures above 20° C. the acetaldehyde monoperacetate decomposes readily yielding acetic acid. Straight thermal decomposition of the α,β-unsaturated aliphatic aldehyde peroxy intermediates, such as methacrolein monopermethacrylate and acrolein monoperacrylate does not selectively give high yield of the respective acrylic and methacrylic acids and in addition the rate of reaction is low.

To date no commercially successful process has been developed for the preparation of acrylic acid or methacrylic acid involving the autoxidation of the corresponding α,β-unsaturated aldehyde and the conversion of the co-produced peroxide intermediate.

The acrylic and methacrylic acid products obtained by the process of this invention have many known commercial uses, particularly for the preparation of esters such as methyl methacrylate and as monomers for polymer formation.

A particular advantage of the process of the present invention is the discovery that catalytic amounts of tellurium per se, organic and inorganic tellurium compounds or mixtures thereof permit the respective peroxide (peroxy) compounds formed by the autoxidation of the unsaturated aldehyde to be selectively decomposed or converted to the acid, e.g., methacrolein monopermethacrylate to methacrylic acid providing an overall process advantage in the liquid phase autoxidation of the aldehyde to produce the desired unsaturated acid.

SUMMARY OF THE INVENTION

According to the present invention there is provided a much improved process for the decomposition of unsaturated peroxide (peroxy) intermediate compounds resulting from the autoxidation of the unsaturated aldehydes, acrolein and methacrolein, by converting the respective co-produce peroxides in the oxidate after the autoxidation step to its corresponding unsaturated carboxylic acid, acrylic or methacrylic, at a suitable temperature in the presence of a catalytic amount of a tellurium catalyst or mixtures thereof.

It is a primary object of this invention to provide a process for the liquid phase preparation of acrylic acid from acrolein or methacrylic acid from methacrolein in high yield by converting or decomposing resulting by-product peroxide compounds to the acid and to avoid operational problems associated with prior processes.

It is another object of this invention to provide a novel reaction system useful in the conversion or decomposition of co-produced peroxide intermediate compounds to the desired acid produced by the autoxidation.

It is a further object of this invention to provide a specific mechanism for the employment of tellurium catalysts for the conversion of peroxide compounds to unsaturated acids.

These and other objects and advantages of this invention will become apparent from the description of the invention which follows and from the claims.

DESCRIPTION OF THE INVENTION

According to the invention a process has been discovered in which high yield of $\alpha,\beta$-unsaturated aliphatic carboxylic acids, i.e., acrylic or methacrylic acid, may be obtained from the autoxidation of the corresponding $\alpha,\beta$-unsaturated aliphatic aldehyde, i.e., acrolein or methacrolein wherein intermediate unsaturated peroxides are co-produced. Principally, the invention comprises a process of separately and catalytically decomposing the unsaturated peroxide compounds, after autoxidation of the aldehyde, at a suitable temperature in the presence of tellurium and/or tellurium compounds thereof to obtain increased yield of the acid and avoid the formation of undesired amounts of polymer. After the autoxidation of the unsaturated aldehyde the co-produced peroxide compounds are catalytically decomposed in the oxidate and the oxidate further processed to recover total product acid.

The oxidate including the intermediate peroxide compounds which may be treated according to this invention may be prepared by the oxidation, in the liquid phase, of acrolein or methacrolein to produce acrylic or methacrylic acid. Any method for the preparation of the acids which co-produces the peroxide intermediates may be employed which results in a liquid phase containing any unreacted aldehyde (acrolein or methacrolein), acid product (acrylic or methacrylic acid), peroxides of the aldehyde and the acid (acrolein monoperacrylate and peracrylic acid, and methacrolein monopermethacrylate and permethacrylic acid) together with other by-products such as acetic acid. The unreacted aldehyde (acrolein or methacrolein) may if desired, be distilled from the oxidate prior to or during the catalytic decomposition of the peroxides.

The oxidation process, to produce the acid and peroxide compounds, may be carried out in the liquid phase on the feed acrolein or methacrolein with or without an inert solvent or catalyst in a suitable reactor at temperatures of from about 0° C. to 100° C. and pressures from about atmospheric to 1500 psig by contacting the aldehyde with oxygen or an oxygen-containing gas, such as described, for example, in U.S. Pat. Nos. 3,114,769, 3,155,719 and 3,253,025. The oxidate produced by such processes may be treated by the process of the present invention to convert the intermediate peroxides to the desired acid.

In any liquid phase oxidation process generally about 30 per cent of the feed acrolein or methacrolein will be converted to the desired unsaturated product acid and the various peroxides produced will generally be present in the resulting oxidate to from about 5 to 30 weight per cent of the total weight of the oxidate.

While lower amounts of polymer formation result from the process of this invention, it is generally desirable, but not essential, to add a polymerization inhibitor to the oxidate solution. Suitable inhibitors include compounds containing an aromatic nucleus such as hydroquinone, pyrogallol, p-methoxyphenol, cresol, resorcinol and phenol, e.g., 2,6-di-tert-butyl-4-methylphenol. The amount of inhibitor added may be between about 0.01 and 1.0 weight per cent of the oxidate.

The tellurium catalysts which may be utilized in the process of this invention are tellurium per se or an organic or inorganic tellurium compound or mixtures thereof. Any organic or inorganic tellurium salt having an anion which does not unduly retard the formation of the desired products by an extraneous side reaction can be utilized as a catalyst to decompose the peroxide intermediates.

Representative tellurium catalysts, in addition to tellurium per se include, for example, inorganic salts such as tellurium nitrate, sulfate, sulfide, disulfide, dichloride, tetrachloride, tetrafluoride, hexafluoride, dirbromide, tetrabromide, tetraiodide, dioxide, trioxide, et. Tellurium oxychloride and oxybromide as well as tellurous acid and telluric acid may be used. Inorganic tellurium salts such as the halides and oxides are particularly preferred, e.g., tellurium tetrabromide and tellurium dioxide. In addition, organic tellurium compounds such as methyl and dimethyl telluride, diphenyl and tetraphenyl telluride, diphenyl and diethyl ditelluride, dimethyl tellurium dichloride, dibromide, diiodide and difluoride, diphenyl telluroxide, phenyl tellurols and 2-chlorocyclohexyltellurium trichloride, etc., may be employed. The preferred organic tellurium catalysts are diphenyl telluride and ditelluride.

Metallic tellurium compounds such as aluminum, zinc, bismuth, copper, lithium, palladium, and lead telluride, etc. may be employed as catalysts in the process of the invention.

The tellurium catalysts may be present in solution or suspension and may also be on support materials which will not affect the decomposition of the peroxide compounds or react with the other products of the oxidate such as alumina, silica gel, aluminosilicates, activated carbon or zeolites. The catalysts may be partially or completely soluble under process conditions and are preferably in a finely divided state.

The decomposition reaction is carried out in the presence of a catalytic proportion of the tellurium catalyst and will proceed with small amounts of the representative compounds or tellurium per se as hereinabove described. Generally the amount of catalyst employed in accordance with the present invention will be equivalent to between about 0.01 and 10 per cent by weight and preferably between about 0.10 and 1.0 per cent by weight of the oxidate reaction mixture containing the peroxide compounds to be decomposed.

While not essential inert organic solvents are generally employed in the decomposition process of this invention. The autoxidation reaction of the unsaturated aldehyde (acrolein or methacrolein) to prepare the corresponding unsaturated carboxylic acids and form the oxidate solution containing the peroxides may employ a solvent and thus the oxidate may already contain a solvent which may be employed directly in the process of this invention provided the solvent is inert under the reaction conditions used; additional inert solvent may also be added. If the solvent contained in the oxidate is not inert but reactive under the certain decomposition reaction process conditions, the solvent may be removed, for example, by distillation and a non-reactive (inert) solvent added, and the mixture subjected to catalytic decomposition by the process of this invention.

The solvents employed in the process of the invention are preferably easily separable from the reaction mixture and components thereof including the unreacted aldehyde starting material, any intermediate products and acid product. The solvents which may be employed in concentrations of from about 10 to 95 weight per cent, preferably 20 to 80 weight per cent of the solvent-oxidant mixture and suitable for use in the process of the present invention can be aliphatic, cycloaliphatic and aromatic hydrocarbons and halogenated hydrocarbons including halogenated aromatic hydrocarbons, carboxylic acids, ethers, esters and amides. Certain inert tertiary alcohols such as tertiary octyl alcohol, and small amounts of primary and secondary alcohols in admixture with the other solvents, e.g., up to about 40 per cent by weight of the solvent mixture, may also be employed. Representative solvents especially suitable for use in this invention include benzene, toluene, o-, m-, and p-xylenes, hexane, cyclohexane, ethylcyclohexane, pentane, chlorobenzene, bromobenzene, chlorotoluene, carbon tetrachloride, chloroform, methylene chloride, acetic acid, ethyl acetate, butyl acetate, methyl acetate, cyclohexyl acetate, methyl benzoate, tetrahydrofuran, dioxane, dimethylformamide, N,N'-dimethyl acetamide, 1,2-dichlorotetrafluoroethane, etc. Mixtures of solvents may be employed, however, it is preferable to use individual solvents in order to lessen any recovery problems.

The process for the catalytic decomposition of the peroxides contained in the oxidate solution may be carried out at temperatures of from about ambient (about 25° C.) to 100° C. and preferably at temperatures of from about 30° C. to 60° C. The process may be conducted at atmospheric, sub-atmospheric or superatmospheric pressures. However, atmospheric pressure is preferred and provides the best result.

The process of the invention may be carried out batchwise, semi-continuous or continuous in any suitable reactor. A general procedure for carrying out the process of the invention is to add the catalyst to the oxidate reaction product containing the peroxide (peroxy) compounds and heat the mixture to the desired temperature for the appropriate period. The reaction products, after decomposition of peroxides, may be recovered and treated by any conventional method such as, for example, by distillation, by extracting the acid with a base and subsequent acidification, or by solvent extraction.

The reaction time to catalytically decompose the peroxide compounds to the respective unsaturated acid may vary between a few minutes and several hours and is generally dependent on the peroxide being decomposed, temperature of reaction and whether the process is continuous or batch.

The following examples are provided to illustrate the invention in accordance with the principles of this invention but are not to be construed as limiting the invention in any way except as indicated by the appended claims. Unless otherwise noted, percentages are in terms of per cent by weight.

In the Examples which follow, the feed material for the catalytic conversion of the peroxide (peroxy) compounds to the acid (acrylic or methacrylic) by the process of the invention was obtained by the autoxidation of acrolein or methacrolein in the absence of added catalyst. The unsaturated aldehyde (acrolein or methacrolein) was charged to a suitable reactor (polytetrafluoroethylene-lined reactors, stainless stell autoclave or aluminum reactor) along with a solvent. The mixture was stirred and heated at 45° C. under a pressure of 200 psig oxygen. Oxygen was added whenever there was a 5 psig pressure drop. After 40 psig of oxygen was reacted, the mixture was cooled and the pressure slowly vented. The reaction product (oxidate) and a wash solvent was recovered from the reactor and 0.1 g. of 2,6-di-tert-butyl-4-methylphenol as a plymerization inhibitor added. The oxidate was then subjected to a catalytic decomposition of the peroxides by the process of this invention.

Analysis of the oxidate solution and the decomposition reaction product solutions were conducted as follows: Samples were titrated by differential potassium iodide to determine permethacrylic acid and methacrolein monopermethacrylate or peracrylic acid and acrolein monoperacrylate. Samples were also reduced with triphenylphosphine and analyzed by gas-liquid chromatography to determine any methacrolein or acrolein content, as well as methacrylic or acrylic acid and acetic acid content.

In the Examples the following abbreviations are used:
TBA — tertiary butyl alcohol
MA — methacrolein
MAA — methacrylic acid
PMAA — permethacrylic acid
MMPM — methacrolein monopermethacrylate
$C_6H_{10}TeCl_4$ — 2-chlorocyclohexyltellurium trichloride
$(C_6H_5)_2Te_2$ — diphenyl ditelluride
$(C_2H_5)_2Te$ — diethyl telluride
$(C_6H_5)_2Te$ — diphenyl telluride

EXAMPLES 1-6

An oxidate containing a mixture of unreacted methacrolein, permethacrylic acid, methacrolein monopermethacrylate, n-pentane solvent, acetic acid, methacrylic acid product and minor amounts of other by-products such as acetic acid, were prepared by charging methacrolein and n-pentane solvent to a 700 ml. aluminum reactor equipped with a stirrer. The mixture was stirred and heated to 45° C. under 200 psig air. After 5 psig of pressure drop, oxygen was added to the reactor. After completion of the reaction, the reactor was cooled and vented and the reaction product oxidate washed with 46 g. of n-pentane solent (providing 98 g. total solvent). 0.5 g of 2,6-di-tert-butyl-4-methylphenol was added to inhibit any polymerization. In Examples 1 to 5, 80.4 g. portions of the reaction product oxidate which contained a tellurium catalyst, 15.8 weight per cent methacrolein, 0.83 weight per cent permethacryylic acid, 2.30 weight per cent methacrolein monopermethacrylate, 3.30 weight per cent methacrylic acid, 77.6 weight per cent n-pentane and minor amounts of other by-products including acetic acid (<0.2 weight per cent) were distilled at 0° C. bath temperature under 15 torr of pressure to give 65 g. of distillate (containing 6.5 g. of methacrolein and 78.5 g. of n-pentane) and 15.6 g. of residue. The residue was heated to the desired temperature in the presence of a certain weight per cent of the tellurium catalyst based on the oxidate solution, to decompose the contained peroxide compounds. An equal portion of oxidate solution residue (Example 6) was heated in the absence of catalyst for comparison. The results are summarized in Table 1.

TABLE 1

CATALYZED DECOMPOSITION OF PEROXIDE COMPOUNDS n-PENTANE SOLVENT

| Ex. | Catalyst (Wt. %) | Temp. °C. | Time hr. | % MMPM Conv. | % MA[1] Conv. | % Selectivity to[3] MMPM | PMAA | MAA | Other By-Products |
|---|---|---|---|---|---|---|---|---|---|
| 1 | $TeO_2$ (1.0) | 45 | 3 | 46 | 28 | 30 | 1 | 55 | 14 |
| 2 | $TeO_2$ (.50) | 55 | 3 | 47 | 27 | 27 | 2 | 58 | 13 |
| 3 | $TeO_2$ (1.0) | 45 | 3 | 52 | 28 | 28 | 1 | 52 | 19 |
| 4 | $TeBr_4$ (1.0) | 50 | 4 | 43 | 27 | 28 | 3 | 55 | 14 |
| 5 | $C_6H_{10}TeCl_4$ (1.0) | 50 | 4 | 61 | 26 | 20 | 2 | 56 | 22 |
| 6[2] | none | 50 | 3 | 27 | 20 | 36 | 6 | 32 | 26 |

[1]% methacrolein conversion, total including autoxidation and peroxide decomposition.
[2]Comparative - no catalyst added.
[3]Total % selectivity to products including autoxidation and peroxide decomposition.

EXAMPLE 7

The procedure of Example 1 for autoxidation was repeated using acrolein to form an oxidate containing a mixture of unreacted acrolein, peracrylic acid, acrolein monoperacrylate, n-hexane solvent (98 g. total after wash) and minor amounts of other by-products including acetic acid. A 5.0 g. portion of the original oxidate containing 11.8 millimoles peracrylic acid and 36.4 millimoles of acrolein monoperacrylate was heated with stirring to 55° C. on a constant temperature bath for 3 hours in the presence of 0.60 weight per cent concentration of tellurium dioxide. Analysis of the oxide after the decomposition reaction showed a 90 per cent peroxide decomposition with a 90 per cent selectivity to acrylic acid.

EXAMPLE 8

The procedure of Example 1 for the autoxidation of methacrolein to form an oxidate was repeated with the exception that n-hexane was used as the oxidation and wash solvent to recover the oxidate reaction product from the autoclave. A 3.0 g. portion of the oxidate containing n-hexane solvent and 1.43 millimoles of PMAA and 47.20 millimoles of MMPM was heated with stirring to 50° C. for 2 hours in the presence of 0.567 per cent by weight of diphenyl telluride. Analysis of the decomposition product showed a 58 per cent peroxide conversion with a 72 per cent selectivity to MAA.

EXAMPLES 9-19

A number of oxidate solutions resulting from the autoxidation of methacrolein or acrolein were prepared by the procedure of Example 1 employing various solvents and mixtures of solvents and 0.5 g. of 2,6-di-tert-butyl-4-methylphenol added to inhibit any polymerization. In Examples 9 to 19, 90.0 g. portions of the reaction product oxidates, unless otherwise noted, were distilled at 0° C. under 15 torr pressure to remove between 60 and 85 per cent of the unreacted methacrolein or acrolein and solvent from the oxidate avoiding explosive tendencies of the peroxides and any non-selective thermal decomposition thereof. Tellurium catalyst was added to the oxidate residue containing the remaining methacrolein or acrolein and solvent and the mixture heated on a constant temperature bath for 3 hours to catalytically decompose the peroxide compounds and the reaction products analyzed. A run was also carried out in the absence of catalyst for comparison. The results are summarized in Table 2.

TABLE 2

CATALYTIC PEROXIDE CONVERSION-DISTILLATION OF UNREACTED ALDEHYDE

| Ex. | Solvent (g.) | Temp. °C. | Catalyst | Catalyst Concentration Wt. %[1] | Peroxides in Oxidate (millimoles) MMPM | PMAA | % Peroxide Decomposition | % MA Con.[2] version | % MAA Selectivity |
|---|---|---|---|---|---|---|---|---|---|
| 9 | n-pentane (7.0) | 45 | Te | 0.50 | 36.0 | 14.0 | 70 | 24 | 94 |
| 10[4] | benzene (7.0) | 25 | $TeO_2$ | 0.75 | 36.0[4] | 14.0[4] | 90[4] | 25 | 82 |
| 11 | n-hexane (7.0) | 55 | $TeCl_4$ | 1.50 | 36.0 | 14.0 | 85 | 20 | 86 |
| 12 | cyclohexane (7.0) | 60 | $(C_6H_5)_2Te_2$ | 0.50 | 36.0 | 14.0 | 88 | 22 | 86 |
| 13 | n-hexane/TBA (7.0/1.0) | 50 | $TeO_2$ | 1.0 | 37.2 | 14.1 | 88 | 26 | 76 |
| 14[4] | xylene (7.0) | 50 | $(C_2H_5)_2Te$ | 0.83 | 36.8[4] | 13.7[4] | 86[4] | 26 | 73 |
| 15 | cyclohexane/$CCl_4$ (8.0/2.0) | 45 | $H_2TeO_3$ | 1.40 | 37.9 | 12.1 | 88 | 20 | 80 |
| 16 | n-pentane/dioxane (7.0/1.0) | 50 | $(C_6H_5)_2Te$ | 0.50 | 35.8 | 13.4 | 87 | 25 | 73 |
| 17[3] | n-pentane (7.0) | 50 | none | — | 36.3 | 12.7 | 39 | 24 | 41 |
| 18 | n-pentane (7.0) | 45 | $Bi_2Te_3$ | 0.60 | 37.8 | 11.9 | 89 | 23 | 85 |
| 19[4] | N-pentane (7.0) | 50 | PbTe | 1.00 | 37.8[4] | 11.9 | 78[4] | 25 | 86 |

[1]The concentration was calculated on the basis of the oxidate.
[2]% Methacrolein Conversion based on original autoxidation after decomposition step.
[3]Comparative run - no catalyst added.
[4]Acrolein employed; peroxy compounds are peracrylic acid and acrolein monoperacrylate.

We claim:

1. A process for the preparation of acrylic acid or methacrylic acid which comprises catalytically decomposing the corresponding unsaturated intermediate peroxide compounds peracrylic acid and acrolein monoperacrylate or permethacrylic acid and monopermethacrylate contained in an oxidate solution in the presence of from about 0.01 to about 10.0 percent by weight of the oxidate reaction mixture of a tellurium catalyst selected from the group consisting of elemental tellurium tellurium nitrate, sulfate, sulfide, disulfide, dichloride, tetrachloride, tetrafluoride, hexafluoride, dibromide, tetrabromide, tetraiodide, dioxide, and trioxide, tellurium oxychloride, tellurium oxybromide, tellurous acid, telluric acid, methyl telluride, dimethyl telluride, diphenyltelluride, tetraphenyl telluride, diphenyl ditelluride, diethyl ditelluride, dimethyl tellurium dichloride, dibromide, diiodide and difluoride, diphenyl telluroxide, phenyl tellurols, 2-chlorocyclohexyltellurium trichloride, aluminum telluride, zinc telluride, bismuth telluride, copper telluride, lithium telluride, palladium telluride and lead telluride, at a temperature of from about ambient to about 100° C., said oxidate solution being derived from the liquid phase autoxidation of acrolein or methacrolein, and recovering the acrylic or methacrylic acid.

2. A process according to claim 1 wherein the tellurium compounds are selected from diphenyl telluride, tellurium dioxide, tellurium tetrabromide, tellurium tetrachloride, diphenyl ditelluride, diethyl telluride, tellurous acid, bismuth telluride, lead telluride or 2-chlorocyclohexyltellurium trichloride.

3. A process according to claim 1 wherein from about 0.10 to about 1.0 per cent by weight of catalyst is employed in the oxidate.

4. A process according to claim 1 wherein an inert organic solvent is employed in the oxidate at concentrations of from about 10 to about 95 weight per cent of the solvent-oxidate mixture and is selected from the group consisting of aliphatic, cycloaliphatic and aromatic hydrocarbons, halogenated hydrocarbons, ethers, esters, carboxylic acids, amides or alcohols or mixtures thereof.

5. A process according to claim 4 wherein the concentration of solvent is from about 20 to 80 weight per cent of the solvent-oxidate mixture.

6. A process according to claim 4 wherein the solvent is selected from the group consisting of n-hexane, cyclohexane, n-pentane, xylene, benzene, carbon tetrachloride, dioxane and tertiary butyl alcohol.

7. A process according to claim 1 wherein the decomposition temperature is in the range of from about 30° C. to 60° C.

8. A process according to claim 1 wherein the tellurium catalyst is supported.

9. A process for the preparation of acrylic acid which comprises the steps of:
oxidizing acrolein with oxygen or an oxygen-containing gas in the liquid phase to produce a reaction product oxidate containing unreacted acrolein, peracrylic acid, acrolein monoperacrylate, acrylic acid and other by-products;
adding from about 20 to 80 weight per cent of an aliphatic, cycloaliphatic or aromatic hydrocarbon, ether, carboxylic acid, amide, alcohol or ester solvent to said oxidate to form a solvent-oxidate mixture;
subjecting the solvent-oxidate mixture to a temperature in the range of from about 30° C. to 60° C. in the presence of from about 0.10 to 1.0 per cent by weight of a tellurium catalyst selected from the group consisting of elemental tellurium, tellurium nitrate, sulfate, sulfide, disulfide, dichloride, tetrachloride, tetrafluoride, hexafluoride, dibromide, tetrabromide, tetraiodide, dioxide and trioxide, tellurium oxychloride, tellurium oxybromide, tellurous acid, telluric acid, methyl telluride, dimethyl telluride, diphenyl telluride, tetraphenyl telluride, diphenyl ditelluride, diethyl ditelluride, dimethyl tellurium dichloride, dibromide, diiodide and difluoride, diphenyl telluroxide, phenyl tellurols, 2-chlorocyclohexyltellurium trichloride, aluminum telluride, zinc telluride, bismuth telluride, copper telluride, lithium telluride, palladium telluride and lead telluride, to catalytically decompose peracrylic acid and acrolein monoperacrylate to acrylic acid; and
recovering said acrylic acid produced by said oxidation and catalytic decomposition.

10. A process according to claim 9 wherein unreacted acrolein in the reaction product oxidate is removed by distillation prior to or during the decomposition step.

11. A process for the preparation of methacrylic acid which comprises the steps of:
oxidizing methacrolein with oxygen or an oxygen-containing gas in the liquid phase to produce a reaction product oxidate containing unreacted methacrolein, permethacrylic acid, methacrolein monopermethacrylate, methacrylic acid and other by-products;
adding from about 20 to 80 weight per cent of an aliphatic, cycloaliphatic or aromatic hydrocarbon, ether, carboxylic acid, amide, alcohol or ester solvent to said oxidate to form a solvent-oxidate mixture;
subjecting the solvent-oxidate mixture to a temperature in the range of from about 30° C. to 60° C. in the presence of from about 0.10 to 1.0 per cent by weight of a tellurium catalyst selected from the group consisting of elemental tellurium, tellurium nitrate, sulfate, sulfide, disulfide, dichloride, tetrachloride, tetrafluoride, hexafluoride, dibromide, tetrabromide, tetraiodide, dioxide and trioxide, tellurium oxychloride, tellurium oxybromide, tellurous acid, telluric acid, methyl telluride, dimethyl telluride, diphenyl telluride, tetraphenyl telluride, diphenyl ditelluride, diethyl ditelluride, dimethyl tellurium dichloride, dibromide, diiodide and difluoride, diphenyl telluroxide, phenyl tellurols, 2-chlorocyclohexyltellurium trichloride, aluminum telluride, zinc telluride, bismuth telluride, copper telluride, lithium telluride, palladium telluride and lead telluride, to catalytically decompose permethacrylic acid and methacrolein monopermethacrylate to methacrylic acid; and
recovering said methacrylic acid produced by said oxidation and catalytic decomposition.

12. A process according to claim 11 wherein the unreacted methacrolein in the reaction product oxidate is removed and recovered by distillation prior to or during the decompostion step.

* * * * *